United States Patent [19]

Kuphal et al.

[11] 4,287,422

[45] Sep. 1, 1981

[54] EXAMINATION TABLE FOR A UROLOGICAL X-RAY EXAMINATION APPARATUS

[75] Inventors: Wilko Kuphal, Rueckersdorf; Heinz Wons, Erlangen, both of Fed. Rep. of Germany

[73] Assignee: Siemens Aktiengesellschaft, Berlin & Munich, Fed. Rep. of Germany

[21] Appl. No.: 967,320

[22] Filed: Dec. 7, 1978

[30] Foreign Application Priority Data

Dec. 30, 1977 [DE] Fed. Rep. of Germany ....... 2759079

[51] Int. Cl.$^3$ ...................... G01N 21/00; A61G 13/00
[52] U.S. Cl. ................................ 250/439 R; 250/456; 269/327; 269/328
[58] Field of Search ............... 250/451, 452, 453, 454, 250/456, 439 R; 128/292, 760; 269/327, 328

[56] References Cited

U.S. PATENT DOCUMENTS

| | | | |
|---|---|---|---|
| 1,762,944 | 6/1930 | Allison | 269/327 |
| 1,919,908 | 7/1933 | Schmidt et al. | 269/327 |
| 2,787,506 | 4/1957 | Travisano | 269/328 |
| 3,257,556 | 6/1966 | Boetcker et al. | 269/328 |
| 3,328,024 | 6/1967 | Weil | 269/327 |

FOREIGN PATENT DOCUMENTS 1629669 10/1951 Fed. Rep. of Germany .

Primary Examiner—Alfred E. Smith
Assistant Examiner—Janice A. Howell
Attorney, Agent, or Firm—Hill, Van Santen, Steadman, Chiara & Simpson

[57] ABSTRACT

In an exemplary embodiment, a patient support platform, resting on a frame, can be irradiated in a shadow-free fashion, and is provided with two longitudinally extending support rails for the mounting of accessories, and a collector basin for collecting outflowing contrast medium. To avoid grooves and cracks where fluids can accumulate and make cleaning very difficult, a single-piece, smooth support plate is provided for entirely covering the upper surface and the four lateral edges—adjoining the upper surface—of the patient support platform, and the support rails are moved to the longitudinal sides of the support plate. In addition, the support plate can be provided with a flat depression with marginal edges extending at a shallow angle for minimized attenuation of incident X-rays. The support rails can manifest a T-shaped cross section and can be mounted with the foot of the "T" on the drawn-down lateral edges of the examination table.

8 Claims, 3 Drawing Figures

U.S. Patent     Sep. 1, 1981     4,287,422
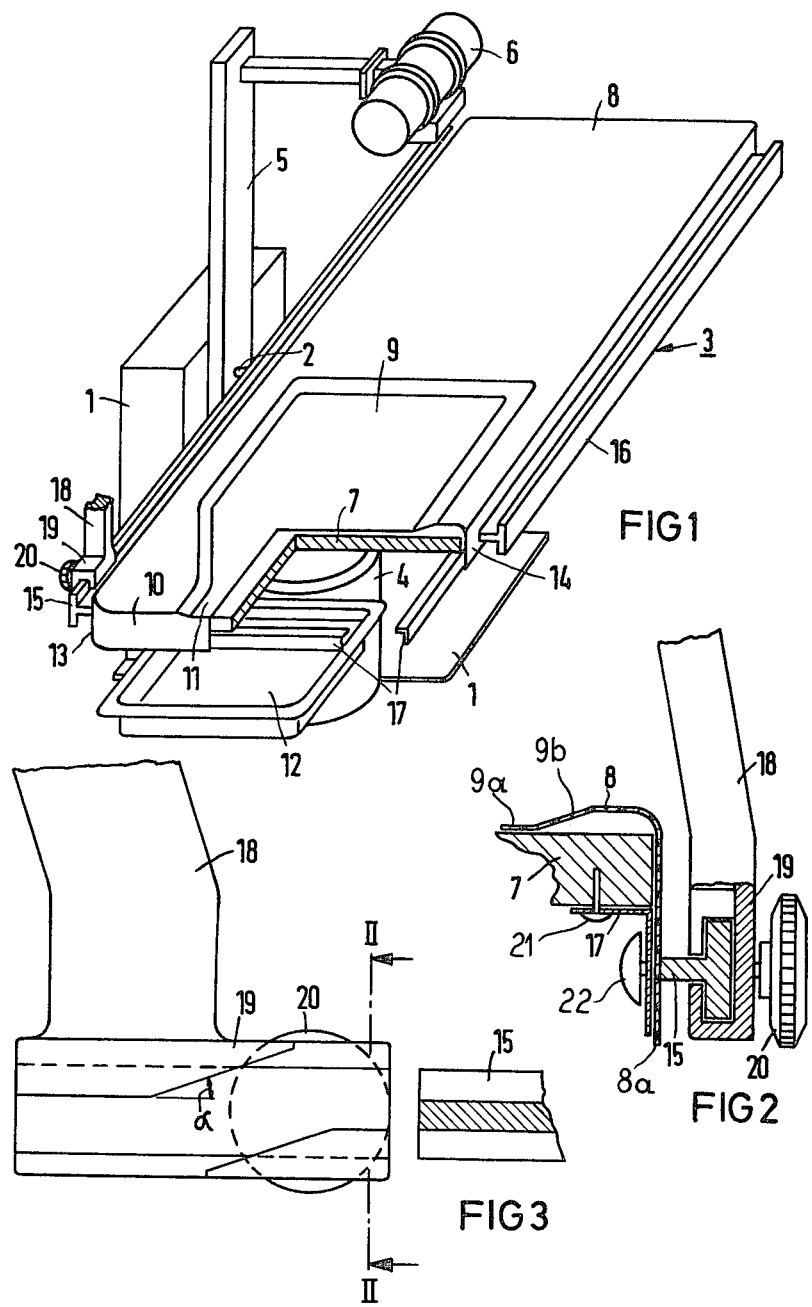

EXAMINATION TABLE FOR A UROLOGICAL X-RAY EXAMINATION APPARATUS

BACKGROUND OF THE INVENTION

The invention relates to an examination table for a urological X-ray examination apparatus comprising a patient support platform capable of shadow-free irradiation, resting on a frame, comprising two support rails for the mounting of accessories, and comprising means for collecting outflowing contrast medium.

In the case of X-ray examination apparatus, it is generally conventional to fabricate the patient support platform of the examination table from plywood panels. Support rails are screwed onto these plywood plates, on the emplacement surface for the patient, at the two longitudinal edges, and support rails contain a longitudinal groove which widens toward the interior. Accessory parts, such as leg holders, arm holders, stands for droppers, etc., can be attached in the support rails. In utilizing patient support platforms of this type for urological X-ray examination apparatus, it is considered disadvantageous that outflowing rinsing (or flushing) fluid and contrast medium run into the cracks between the patient support platform and the screwed-on support rails, as well as into the grooves of the support rails, and can only be removed therefrom with great difficulty.

From the German Gebrauchsmuster 1,629,669, it is already known, to this end, to introduce a U-shaped auxiliary frame into the longitudinally extending support rails of the patient support platform. The open side of this auxiliary frame is closed by an elastic rubber band. A wax-like cloth is inserted into this auxiliary frame. The patient to be examined is situated with his posterior on the wax-like cloth such that the rubber band of the auxiliary frame rests against the back. The slip-on auxiliary frame thus prevents rinsing (or flushing) fluid or outflowing contrast medium from being able to spread over the entire patient support platform. However, it is considered disadvantageous that an additional accessory part has thus been brought about which, following every examination, must be withdrawn from the support rails of the patient support platform, cleansed, and stowed away somewhere. In addition, this additional auxiliary frame cannot prevent the grooves in the support rails from becoming soiled if rinsing fluid or contrast medium is splashed out or inadvertently spilled.

SUMMARY OF THE INVENTION

Accordingly, the object underlying the invention consists in developing an examination table for a urological X-ray examination apparatus which is always simple to cleanse and disinfect. In addition, a solution is to be found whereby no additional accessory part will result which takes up space when put away.

Accordingly, in the case of the examination table of the type initially cited, in accordance with the invention, a one-piece, smooth, support plate comprising support rails attached to the longitudinal sides is mounted onto the patient support platform, such support plate consisting of material which can be readily disinfected, and which fully covers the upper surface and the four lateral edges of the patient support platform adjacent thereto. This has the great advantage that rinsing (or flushing) fluid and contrast medium can be readily wiped off at any time without necessitating an additional accessory part for this purpose. In addition, this construction avoids the occurrence of cracks, slits, or grooves on the support surface for the patient into which the contrast medium can flow.

The smearing of rinsing fluid and outflowing contrast medium can be largely avoided if, in an additional advantageous further development of the invention, the support plate is provided, in the region of the posterior of the patient, with a flat, 1- to 5-mm-deep depression extending flatly at its edges. This provides the additional advantage consisting in that the contrast medium, insofar as—as is normally the case—it drains out only in small quantities, will remain in the region of the flat depression, and later, after the examination, can be easily wiped off with a cloth. It is just as simple to wash off the support surface for the patient including the depression with a disinfectant fluid.

In an expedient embodiment of the invention, the depression can be provided with an outlet port or channel in the region of the caudal end face of the support plate. This provides the advantage that also greater quantities of contrast medium and rinsing fluid can be collected and that they can flow into a collector receptacle commonly arranged at the end of the patient support platform under the same.

In a particularly expedient further development of the invention, the support rails can manifest a T-shaped cross section, and they can be mounted with the foot of the "T" onto the drawn-down sections of the support plate covering the frontal edges of the patient support platform. This has the advantage that the support rails likewise do not possess any groove which are detrimental during cleansing. Rinsing fluid inadvertently running down or contrast medium running down can be wiped out from the T-shaped rails without any particular difficulties. In addition, the T-shaped rails form a channel conduit which prevents laterally overflowing rinsing fluid from being able to run onto the floor.

The carrying capacity of the support rails is substantially improved if the support rails, in an embodiment of the invention, are fastened through the support plate with the frame of the examination table bearing the patient support platform. In addition, the T-shaped rails thus form a suitable means in order to also connect the support plate with the frame of the examination table disposed therebelow.

An attractive appearance of the examination table of the patient support plate can be achieved if the depression, in a top plan view, with the exception of the region of the discharge port, has an essentially rectangular cross section with strongly rounded corners. This design of the depression is not only visually attractive; it also has the advantage that the quantity which can be collected in the depression is enlarged as compared with a circular depression. In addition, through this shaping of the depression with edges running parallel to the longitudinal edges, a surface has been created which is relatively insensitive to slight surface shrinkages of the material of the support plate.

In a particularly advantageous further development of the invention, the foot section of the accessory holders which can be slipped over the support rails can have a C-shaped cross section. In addition, for the locally-independent fitting onto the support rails, such foot section can be milled out in the width of the rail head on the slotted side, at mutually opposite ends, and on oppositely disposed sides of the slot, at an angle $\alpha$ of approximately 30°, and can be provided with a clamping device for engaging the support rails. This makes it possible to slip the support-mountings over the ends of the support rails as well as, after an angular shifting of 30°, to slip them on in the center of the rails and to lock them with the clamping device. By this means, it is possible to also subsequently insert additional support mountings between already present support mountings which have been locked onto a support rail.

Further details of the invention shall be explained in greater detail on the basis of the sample embodiments illustrated in the Figures of the accompanying sheet of drawings; and other objects, features and advantages will be apparent from this detailed disclosure and from the appended claims.

BRIEF DESCRIPTION OF THE DRAWINGS

FIG. 1 shows a graphical representation of the examination table with a portion thereof broken away and in section to better show underlying parts;

FIG. 2 shows a partial sectional view of a support mounting for an accessory part slipped onto a support rail; and FIG. 3 shows a partial view of the foot part of the support mounting from the perspective of the examination table, and a portion of the receiving rail.

DETAILED DESCRIPTION

In FIG. 1, an examination table 3 can be recognized which is mounted onto a pedestal 1 for tilting movement about a horizontal axis 2. The examination table has an X-ray image intensifier 4 arranged beneath the examination table, and an X-ray tube 6 mounted on an X-ray tube carrier 5 above the examination table 3. Examination table 3 consists of a patient support platform 7 with an overlying support plate 8 for the patient which is slipped over the patient support platform. The support plate 8 is fabricated from a synthetic (or plastic) material which can be readily disinfected, in the present instance, a deep-drawable plastic, an acrylonitrile butadiene styrene copolymer, and which is constructed in a single piece. Basically, it could also be fabricated from other thermoplastic (or heat-deformable) plastics such as polyvinyl chloride or polystyrene. The support plate 8, in the region of the one end of the patient support platform 7—at that location where, during examination, the posterior of the patient is placed—is provided with a flat depression 9. This depression is continued in a funnel-shaped outlet port or channel 11 to the caudal frontal side 10 of the examination table 3. Beneath the examination table, a collector basin 12 is mounted in a pull-out fashion in the manner of a drawer beneath the caudal frontal side. On the two longitudinal sides 13, 14, of the examination table, a T-shaped support rail 15, 16, is attached in each instance, resting against the frontal face with the foot end of the "T". These support rails are screwed tightly onto the frame 17 on which the patient support platform 7 also rests.

During the examination of a patient, the patient is placed on the support plate 8 in such a fashion that his posterior comes to rest in the region of the depression 9. In this region, the depression fits closely on the patient support platform 7 as indicated at 9a in FIG. 2. The depression 9 will not be reproduced on the fluoroscopic image, since it manifests a uniform thickness over its entire surface, and its edges such as 9b, FIG. 2, in the region of the depression are so flat (extend at such a shallow angle) that barely appreciably greater radiation paths result through the material of support plate 8. Outflowing contrast medium collects in the region of the depression 9 and can, during the examination, given a horizontally positioned examination table 3, flow only from the caudal frontal side through the funnel-shaped discharge port 11 from the depression 9 into the pull-out collector basin 12 on the caudal frontal side 10 of the examination table 3. This also applies to the rinsing (or flushing) fluid required in the case of some examinations. The contrast medium remaining in the depression can be readily wiped out upon termination of the examination. The support rails 15, 16, at the two longitudinal edges of the examination table 3 act like roof gutters. They prevent inflowing contrast medium from laterally dropping onto the floor. The inflowing contrast medium, however, can readily be wiped out from the support rails with a cloth.

FIG. 2 illustrates in cross-section the mounting of an accessory holder 18, for example, a leg holder, on a support rail 15, and the mounting of the support rails such as 15 on the frame 17 of the examination table 3. The patient support platform 7 and the support rails 15, 16 are independently fastened tightly to frame 17 by means of screws such as 21 and 22 to form the assembled examination table 3. The support rail such as 15, FIG. 2, tightly clamps the edges 8a of the support plate 8 against the frame 17.

The foot parts 19 of the accessory holders 18 are milled out in a C-formation corresponding to the dimensions of the profile of the support rails. Therefore, they can be slipped, from the ends of the support rails, over the latter, and locked at a desired location therealong with a clamping device 20, in the sample embodiment, a screw clamp. The illustration of FIG. 3 shows that the foot parts 19 of accessory holders 18, which have been milled out in a C-formation, have been milled out to the base at an angle $\alpha$ of approximately 30° on the side of the slot in a width which corresponds to the head-width of the T-profile of the support rail. This renders it unnecessary to slip the accessory holders on from the end of the support rails. On the contrary, it is thus possible to also slip the accessory holders over a support rail 15, 16, at a random location, by angularly shifting the accessory holder 18 about the angle $\alpha$, slipping its foot section 19 with the oblique milling-out fitting over the support rail, pivoting the holder back into the upright position, and locking the same in position with the screw clamp 20. This is particularly advantageous if, after several accessory holders have already been attached to the support rails, an additional accessory holder must be subsequently secured between two such accessory holders.

The depression 9, FIG. 1, in top plan view, with the exception of the region of the discharge port 11 has an essentially rectangular cross section with strongly rounded corners. All edges and corners of the support plate 8 are rounded with a radius of at least five millimeters (5 mm).

It will be apparent that many modifications and variations may be effected without departing from the scope of the novel concepts and teachings of the present invention.

We claim as our invention:

1. An examination table for a urological X-ray examination apparatus comprising a patient support platform capable of shadow-free irradiation, resting on a frame, comprising two longitudinally extending support rails for the mounting of accessories, and comprising means for collecting contrast medium flowing out, characterized in that there is mounted on the patient support platform (7) a single-piece, smooth, support plate (8) with support rails (15, 16) attached to the longitudinal sides (13, 14), said support plate consisting of readily disinfectible material, completely covering the upper surface and the four lateral edges of the patient support platform adjoining the upper surface.

2. An examination table according to claim 1, characterized in that the support plate (8) is provided, in the region of the posterior of the patient, with a flat, 1 to 50 mm-deep depression (9) which is flat at its edges.

3. An examination table according to claim 2, characterized in that the depression is provided with a discharge port (11) in the region of the caudal frontal side (10) of the support plate (8).

4. An examination table according to claim 1, with the support rails (15, 16) having a T-shaped cross section, each support rail including an elongated foot portion secured with a respective lateral edge (8a, FIG. 2) of the support plate (8), said lateral edges of the support plate covering the edge of the patient support platform (7) and the frame (17) of the examination table (3), the support rails (15, 16) being fastened through the support plate (8) with the frame (17) of the examination table (3), and the frame (17) bearing the patient support platform (7).

5. An examination table according to claim 2, characterized in that the depression (9), in a top plan view, with the exception of the region of the discharge port (11), has an essentially rectangular cross section with strongly rounded corners.

6. An examination table according to claim 4, characterized in that the foot section (19) of accessory holders (18), which are capable of being slipped over the support rails (15, 16), has a C-shaped cross section, and, for the purpose of locally-independent fitting onto the support rails (15, 16), is milled out in the width of the rail head on the slotted sides, at mutually opposite ends, and on oppositely disposed sides of the slot, at an angle $\alpha$ of approximately 30°, and that it is provided with a clamping device (20) for engaging the support rails.

7. An examination table according to claim 1, characterized in that a deep-drawable thermoplastic synthetic such as e.g. acrylonitrile butadiene styrene copolymer is utilized as the material for the support plate (8).

8. An examination table according to claim 1, characterized in that all edges and corners of the support plate (8) are rounded with a radius of at least 5 mm.

* * * * *